United States Patent
Strong et al.

[11] Patent Number: 6,061,420
[45] Date of Patent: May 9, 2000

[54] METHODS AND APPARATUS FOR GRAPHICAL RX IN A MULTISLICE IMAGING SYSTEM

[75] Inventors: Gary R. Strong, Waukesha; Bob L. Beckett, Wales; Holly A. McDaniel, New Berlin; Kathryn M. Littlejohn, Wales; Steven M. Zanoni, Brookfield, all of Wis.

[73] Assignee: General Electric Company, Milwaukee, Wis.

[21] Appl. No.: 09/139,990

[22] Filed: Aug. 25, 1998

[51] Int. Cl.[7] .................................................. A61B 6/00
[52] U.S. Cl. ................................ 378/4; 378/8; 378/20; 378/901
[58] Field of Search ........................... 378/4, 8, 15, 20, 378/901

[56] References Cited

U.S. PATENT DOCUMENTS

| | | | |
|---|---|---|---|
| 5,175,938 | 1/1993 | Smith | 33/567 |
| 5,673,298 | 9/1997 | Mazess | 378/54 |

*Primary Examiner*—David V. Bruce
*Assistant Examiner*—Allen C. Ho
*Attorney, Agent, or Firm*—Armstrong, Teasdale; Christian G. Cabou; Phyllis Y. Price

[57] ABSTRACT

Methods and apparatus for a multislice graphic Rx display which, in one embodiment, determines a true image location in the Z axis, selects a the correct scan data for image generation, and if a scan is initiated via the GUI or via graphic Rx, determines the affect on the ISO center and DFOV, are described. More particularly, the system determines the offset from the scan plane for each image plane, so that the true image location in Z is displayed. The image offset from the scan plane is a function of the detector row thickness, the number of detector rows, the scan pitch (helical scanning only), the image thickness, and the gantry tilt angle. Further, the image thickness is selected by the user via the GUI, and constrains the image interval which is displayed on the graphic Rx display. Based on image thickness and image interval, the correct scan data is selected so that images are generated at locations exactly matching those shown on the graphic Rx display. Also, if a scan is prescribed either via the GUI or graphic Rx display, the affect on ISO center and DFOV is determined. This information is automatically updated on the graphic Rx display by modifying the cut-line position up/down to show ISO affect and by modifying the cut-line length to show DFOV.

20 Claims, 3 Drawing Sheets

METHODS AND APPARATUS FOR GRAPHICAL RX IN A MULTISLICE IMAGING SYSTEM

BACKGROUND OF THE INVENTION

This invention relates generally to imaging and, more particularly, to prescribing scan parameters for scans in a multislice imaging system.

In at least some medical imaging systems generally known as computed tomograph (CT) imaging systems, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a post patient collimator for collimating scattered x-ray beams received it the detector. A scintillator is located adjacent the post patient collimator, and photo diodes are positioned adjacent the scintillator.

Multislice CT systems are used to obtain data for an increased number of slices during a scan. Known multislice systems typically include detectors generally known as 3-D detectors. With such 3-D detectors, a plurality of two rows of detector elements, and a four slice detector has four rows of detector elements. During a multislice scan, multiple rows of detector cells are simultaneously impinged by the x-ray beam, and therefore data for several slices is obtained.

In single slice systems, a feature generally referred to as graphic Rx (prescription) is utilized to assist a user in prescribing axial, helical or cine scans by showing "cut" lines" superimposed on one or more scout images. The "cut" lines describe the image location, image interval, image display field of view (DFOV), image center in the X/Y plane, and image tilt. The graphic Rx controls are provided through a bidirectional interface with a text based graphical user interface (GUI) so that changes to key scan parameters made in one mode (e.g., the graphic Rx mode) are automatically updated in the other (e.g., text based GUI mode).

For single slice scanning display, and in the graphic Rx mode, the image center locations which correspond to the scan center locations and the laser light position are displayed. This relationship simplifies translations from scan and reconstruction parameters. For example, the following relationship exists in single slice scanning:

laser light position=scan plane location=image plane location

In multislice scanning, however, and since there is only one scan plane but multiple detector rows, the following relationship exists:

laser light position=scan plane location (not=) image plane location.

In addition, graphic Rx is impacted by the ability of the user to select various image thickness options, and the number of images per gantry rotation, as reconstruction parameters. Also, the ISO centers of tilted scans are offset up/down due to the detector rows physically being offset above and below the true ISO center. This offset is corrected algorithmically, impacting the image ISO center and maximum field of view.

In spite of the differences between single slice and multislice image display, it would be desirable to provide a graphic Rx mode in a multislice imaging system to assist a user in prescribing axial, helical or cine scans.

BRIEF SUMMARY OF THE INVENTION

These and other objects may be attained by methods and apparatus for multislice graphic Rx which, in one embodiment, determine a true image location in the Z axis, select a the correct scan data for image generation, and if a scan is initiated via the GUI or via the graphic Rx mode, determine the affect on the ISO center and DFOV. More particularly, the system determines the offset from the scan plane for each image plane so that the true image location in Z is displayed. The image offset from the scan plane is a function of the detector row thickness, the number of detector rows, the scan pitch (helical scanning only), the image thickness, and the gantry tilt angle.

Further, the image thickness is selected by the user via the GUI, and constrains the image interval which is displayed on the graphic Rx display. Based on image thickness and image interval, the correct scan data is selected so that images are generated at locations exactly matching those shown on the graphic Rx display. Also, if a scan is prescribed either via the GUI or graphic Rx display, the affect on the ISO center and DFOV is determined. This information is automatically updated on the graphic Rx display by modifying the cut-line position up/down to show the ISO affect and by modifying the cut-line length to show the DFOV.

DETAILED DESCRIPTION OF THE INVENTION

Set forth below is a description of an exemplary multislice CT system. Graphic Rx apparatus and methods for such system are then described. Although one embodiment of a multislice system is described in detail below, it should be understood that the graphic Rx methods and apparatus in accordance with the present invention can be utilized in connection with many different multislice systems.

Figure 1:
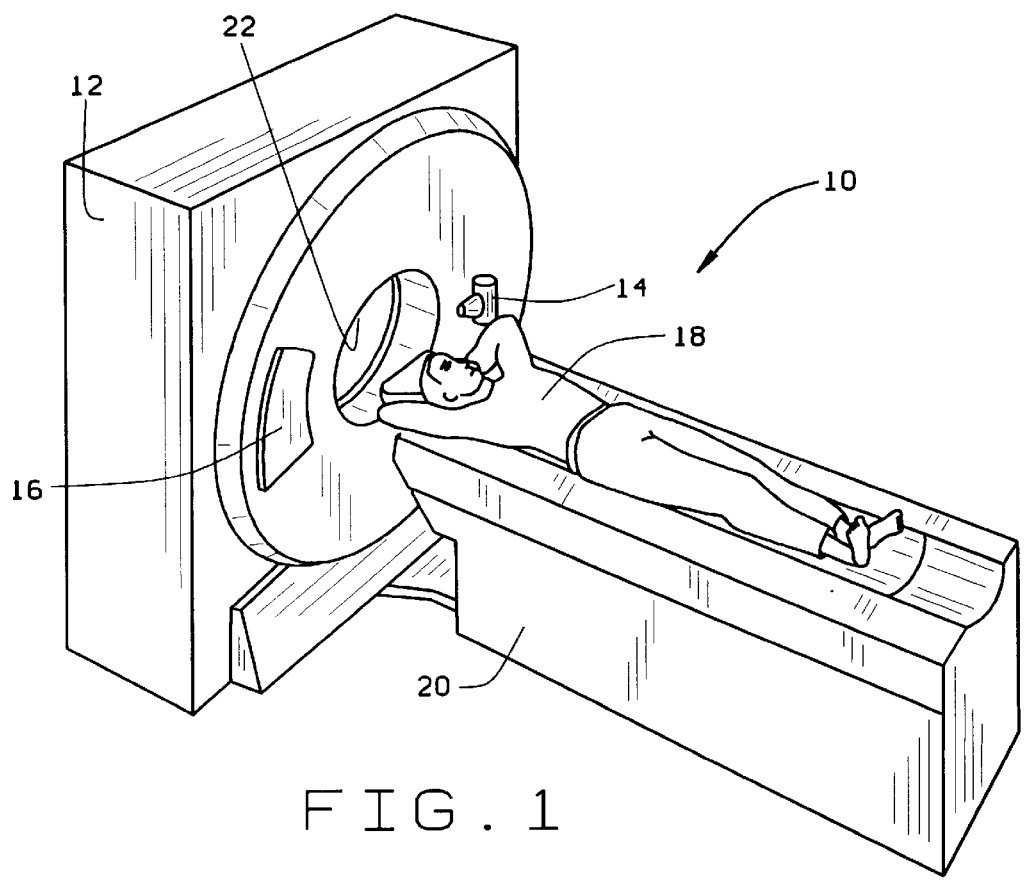
FIG. 1 is a pictorial view of a CT imaging system.

Referring now to FIG. 1, a computed tomography (CT) imaging system 10 in accordance with one embodiment of the present invention is shown as including a gantry 12 representative of a "third generation" CT scanner. Gantry 12 has an x-ray source 14 that projects a beam of x-rays toward a detector array 16 on the opposite side of gantry 12. Detector array 16 is formed by a plurality of detector modules which together sense the projected x-rays that pass through a medical patient 18. Each detector module produces an electrical signal that represents the intensity of an impinging x-ray beam and hence the attenuation of the beam as it passes through patient 18.

During a scan to acquire x-ray projection data, gantry 12 and the components mounted thereon rotate about a center of rotation. A motorized table 20 positions patient 18 relative to gantry 12. Particularly, table 20 moves portions of patient 18 through a gantry opening 22 during a scan.

Figure 2:
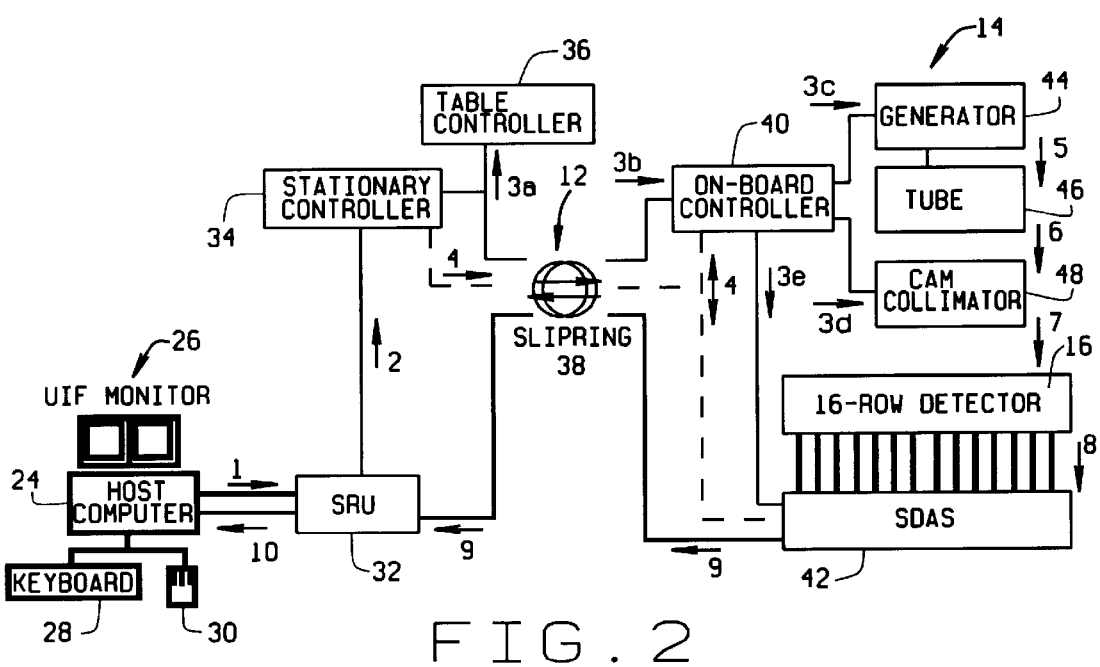
FIG. 2 is a block schematic diagram of the system illustrated in FIG. 1.

FIG. 2 is a block schematic diagram of the system illustrated in FIG. 1. As shown in FIG. 2, system 10 includes a host computer 24 coupled to a monitor (user interface) 26 for displaying images and messages to an operator. Computer 24 also is coupled to a keyboard 28 and a mouse 30 to enable the operator to input information and commands to computer 24. Computer 24 is coupled to a scan and reconstruction control unit (SRU) 32. SRU 32 also includes image generation controls. In one specific embodiment, SRU 32 includes a SGI PCI-based central processing unit which operates on an IRIX operating system. SRU 32 also includes an interface processor for interfacing with the data acquisition system, and a scan data correction digital signal processing board for performing preprocessing, which is known in the art. SRU 32 also include an image generator for filtered backprojection and postprocessing operations, as is known in the art.

A stationary controller 34 is connected to SRU 32, and controller 34 is coupled to a table controller 36. Stationary controller 34 also is connected, through a slipring 38, to an on-board controller 40 and a scalable data acquisition system (SDAS) 42. A slipring 38 enables contactless transmission of signals across the slipring boundary and supports the necessary bandwidth for transmission of data and commands across the boundary. SDAS 42 samples and acquires the data from detector 16 and converts the sampled analog signals to digital signals. SDAS 42, in the specific embodiment, includes forty eight interchangeable converter cards to support four row data acquisition. For two row data acquisition, twenty four cards could be used. In this specific embodiment, there are sixty four input channels per converter card and 1408 Hz sampling can be performed. SDAS 42 also includes a front-end pre-amplifier for amplifying the signals. A forward error correction is applied to the output data.

On-board controller 40 controls operation of x-ray source 14 and operation of SDAS 42, which converts analog signals to digital data as described above. X-ray source 14 includes a high voltage generator 44 coupled to an x-ray tube 46. Tube 46 may, for example, be the tube known in the art is the Gemini-1 tube and currently utilized in at least some CT system commercially available from General Electric Company, Milwaukee, Wis., 53201. Beams projected by X-ray tube 46 pass through a prepatient cam collimator 48 and impinge upon detector 16 (illustrated as a 16 row detector). Cam collimator 48 also is controlled by on-board controller 40. Outputs from detector 16 are supplied to SDAS 42.

With respect to operation of system 10, and in FIG. 2 data flow is illustrated by bold lines, control flow is illustrated by normal lines, and real-time control flow is illustrated by dotted lines. The numeric identifiers associated with the flows are set forth below.

1: scan and reconstruction prescription from operator
2: scan prescription to "master" controller
3: scan parameters distributed
   3a: table position
   3b: rotating parameters
   3c: kV and mA selections
   3d: x-ray beam collimation and filter selections
   3e: detector slice thickness and SDAS gain selections
4: real-time control signals during scanning
5: high voltage
6: un-collimated x-ray beam
7: collimated x-ray beam
8: analog scan data
9: digital scan data
10: patient images Generally rotation of gantry 12 and the operation of x-ray source 14 are governed by controller 34. On-board controller 40, under the control of stationary controller 34, provides power and timing signals to x-ray source 14. SDAS 42 samples analog data from detector 16 and converts the data to digital signals for subsequent processing. SRU 32 receives sampled and digitized x-ray data from SDAS 42 and performs high speed image reconstruction. The reconstructed image is applied as an input to computer 24 which stores the image in a mass storage device.

Computer 24 also receives commands and scanning parameters from an operator via keyboard 28 and mouse 30 Monitor 26 allows the operator to observe the reconstructed image and other data from computer 24. The operator supplied commands and parameters are used by computer 24 to provide control signals and information. In addition, controller 36 controls motorized table 20 to position patient 18 (FIG. 1).

Generally, the above described CT system is operable to collect 1, 2 or more slices data. Axial, helical, and cine scans can be performed with the system, and cross section images of a scanned object can be processed, reconstructed, displayed and/or archived. Scalable axial image reconstruction and display refers, for example, to selectability of the image thickness, number of slices, and number of images to be displayed. Further, the system is not limited to practice with any one particular image reconstruction algorithm, and it is contemplated that many different reconstruction algorithms can be utilized. Exemplary algorithms are set forth in U.S. Pat. Nos. 5,469,487, 5,513,236, 5,541,970, 5,559,847, and 5.606,585, and in co-pending U.S. patent application Ser. Nos. 08/561,382 (filed Nov. 21, 1995), 08/779,961 (filed Dec. 23, 1996), and 08/797,101 (filed Nov. 26, 1997), all of which are assigned to the present assignee, and all of which are incorporated herein, in their entirety, by reference.

In the axial multi-slice scan mode, multiple rows of scan data can be processed before image reconstruction, and the data can be used to produce either multiple thin slices or a reduced number of thicker slices with reduced image artifact. In addition, images with thicker slice thicknesses can be later reconstructed retrospectively into thinner slices of images based on clinical diagnosis needs. As a result, the number of unwanted images for viewing, filming, and archiving is reduced, In addition, high z-axis resolution images can be later reconstructed for patient diagnosis.

In the helical multi-slice scan mode, multiple combinations of patient table speed and x-ray beam and detector collimations, enable generation of images having different z-axis resolution can be produced. For example, at the table speed of 30 mm/rotation, images of 5–10 mm slices can be generated. Thicker slice (such as 10 mm) images can be generated prospectively, which provides the benefit of a reduced number of images and reduced image reconstruction time. At a later time, thinner slice images can be generated retrospectively using the same data. Such thinner slice images may be necessary depending on the clinical-application needs. Such thinner slice images can be generated without rescanning the patient.

Figures 3, 4:
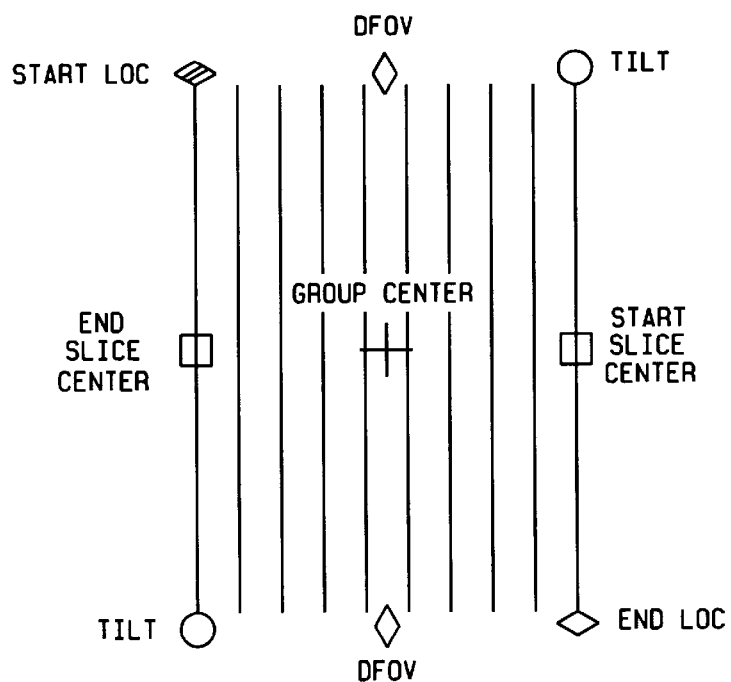
FIG. 3 is an exemplary embodiment of a scan user interface than can be used in conjunction with the system illustrated in FIGS. 1 and 2.
FIG. 4 is an exemplary handle layout.

FIG. 3 is an exemplary embodiment of a scan user Interface than can be used in conjunction with the system illustrated in FIGS. 1 and 2. The interface would be implemented in an instruction set stored in host computer 24 (FIG. 2) and displayed on the host computer monitor. At the scan user interface, an operator can select the scan mode, i.e,. helical or axial, as well as the various scan parameter associated with each mode. The selections are made, for example, by the user by simply touching the desired area corresponding to the desired parameters. Touch sensitive interfaces are well known. Of course, many other types of interfaces could be used, and the interface illustrated in FIG. 3 is only an exemplary interface.

In the helical mode, the operator selects the desired slice thickness, the scan mode, and the scan speed. The "Hi-Q" scan corresponds to a high image quality scan and the "Hi-Speed" scan corresponds to a fast patient table speed. In the axial scan, the operator selects the desired slice thickness and the number of image to be generated per rotation.

Further details regarding the above described multislice CT system are set forth in copending U.S. patent application Ser. No. (15-CT-4641) entitled Scalable Multislice Imaging System, which is assigned to the present assignee and incorporated herein, in its entirety, by reference.

GraphicRx, as used herein, refers to prescribing axial or continuous (helical or cine) scans on a scout image displayed on monitor 26, and enables the user to see exactly where an image will be reconstructed from with respect to the patient anatomy. The cutlines displayed are actually the center of the image locations.

In the above described CT system, the graphicRx function may be provided in a toggle state on host computer 24 and selected by the user on monitor 26. When the state is selected, cutlines are displayed on a 1024 scout display. The scout displayed is a scout image from the same exam, with the same landmark identifier as is currently prescribed. When selected, the scout and the cutlines from all groups in the scan protocol are shown. If no groups have been defined, two cutlines with graphicRx handles are shown on the scout. The scout displayed in the graphicRx window is the same scout displayed in the real time scout window. If no scout exists in the real time scout window, the image selections are searched for a valid scout to display. If the search fails to locate a valid scout, then the last displayed scout for graphicRx is displayed if valid. If the scout is from the real time scout window, window and level are carried over from the real time scout window to the graphicRx window. If the scout comes from the search selections, default window and level values are used. If the scout is the last graphicRx scout displayed, the last window and level displayed in the graphicRx viewport is used.

Adjustments are made using the mouse and image handles on the graphicRx display. These adjustments are made by selecting single or multiple groups, by clicking with mouse 30. To adjust groups, the operator presses and holds the left mouse button on the desired graphic parameter. Handles on the cutlines serve as the mechanism for graphically manipulating the prescription. A handle layout is illustrated in FIG. 4. The following functions can be performed graphically 1. Select 1 or multiple groups
2. Add/delete slices—moving the start or end handle adds slices to that side of the group. The additional slices are not added in a symmetrical manner The slices are only added to one side ("anchor" at opposite side). Moving the start or end handle with the <Shift> key selected adds/deletes slices symmetrically. That is, the slices are added/deleted to both sides ("anchor" at center). The start handle is filled to distinguish it from the end handle. The start handle appears on the cutline located at the prescribed starting location.
3. Adjust DFOV—moving either of the DFOV handles causes the DFOV to increase or decrease in a symmetrical fashion ("anchor" at group center). Moving either DFOV handles with the <Shift> key selected causes the DFOV to increase or decrease in a non-symmetrical manner ("anchor" at opposite side).
4. Adjust gantry tilt—two handles are available for prescribing gantry tilt. These handles are not be visible (or active) when an AP scout is displayed.
5. Adjust RAS (Right Anterior Superior) center (group center)—"Anchor" at the handle (at the group center). Adjustment of RAS center with the <Shift key > selected is not anchored.

Handles only appear on 1 group, even if multiple groups are selected. If multiple groups are selected, handles appear on the first group selected.

When any adjustments are made, the view/edit table is updated. The update to the view/edit table occurs only when the adjustment is stopped, not during manipulation. While adjustments are being made on the graphicRx display, no information can be simultaneously entered into the view/edit table.

The operator performs these adjustments on single or multiple groups. If more than one group is selected, adjustment to DFOV, gantry tilt, RAS center and start and end location are simultaneously applied to all of the selected groups. Adjustment to add/delete slices affects only the primary selected group.

With respect to group selection, the term "primary selected group" refers to the selected group which displays the handles. Selected groups appear in the selected color (e.g., cyan). Deselected groups appear in the deselected color (e.g., white). All groups may be selected when the graphicRx mode is started. The group with the handles (primary selected group) is the first group as specified in the protocol. The view/edit table highlights the image number column of the primary selected group.

With respect to multiple group adjustment, the group with handles is the primary selected group. With multiple groups selected, any adjustments to a primary selected group DFOV, RAS center, gantry tilt or start and end location parameters are applied simultaneously to the same parameter of all the selected groups. Adjustment to the primary group start and end location parameters are only applied to the selected groups if the adjustment is made through the RAS center handle.

With multiple groups selected, any adjustment to a primary group number of slices parameter shall not be applied to the same parameter of all the selected groups. While adjusting, the following information is shown (real-time) in a popup: start location, end location, gantry tilt, DFOV, r/l center, a/p center, a/p center number of images All parameters displayed are parameters of the primary selected group.

With single group adjustment, the following information is shown (real-time) in a popup: start location, end location, gantry tilt, DFOV, r/l center, a/p center and number of images. All parameters are parameters of the selected group.

If two scout scans have been performed, graphicRx may be performed on either scout so long as the scout is a valid scout. The operator can change the scout displayed using the next/prior command or the image list select accelerator line command.

The following functions may be performed within the view/edit table:
   delete/add a group,
   delete all groups
   change the primary selected group (group displaying handles)
   add slices to a group containing one and only one slice The user may graphically prescribe up to, for example, 450 slice locations (this limit is set by the number of raw data files). If only one cutline exists in the group, the only handles present are the group center, gantry tilt and DFOV handles 90° and 270° scouts and the group center and DSFOV handles on 0° and 180° scouts. Tick marks may be shown on the center of each slice, normal to the slice. The length of the tick marks indicates the slice thickness. The length of the cutline indicates the DFOV.

For gantry tilt, an angle measured within ±30° maximum from vertical is allowed. This angle is translated into a gantry tilt and is based on patient orientation. A positive tilt value results in the gantry being tilted towards the superior. A negative tilt value results in the gantry being tilted toward the inferior. Adjusting gantry tilt is available on a scout that has a plane of 90° or 270°.

In a multi-slice scanner, the tilted gantry axis and the patient axis are not in the same plane and do not intercept each other. This introduces three sets of problems—the gantry axis shift ($Y_{Shift}$) from the patent axis, a discrepancy between the beam space and the slice position along the patient axis (Z-axis), and distortion in Y axis.

Table position is defined as the distance between the center of x-ray beam and zero position which is set by operator Because two slices or four slices of images are obtained for each table position, table position and slice position are not equal in twin or quad systems. The table position is shown in the gantry panel and in the console display.

The inner alignment light position is set to the same position as the table position (center of beam in z-axis or center of detector in z-axis). The external alignment light position is the same as in a single slice system and need not be adjusted.

Slice Position is the location of the beam center position from the gantry plane for each slice. Slice position (SP) is calculated from the slice thickness (T), and is added to the information of image data and raw data. The slice position for a four row detector is determined in accordance with:

(Head first into gantry)->$SP=\{[-1.5, -0.5, 0.5, 1.5]*T\}$=Table Position (1)

(Feet first into gantry)->$SP=\{[-1.5, -0.5, 0.5, 1.5]*T\}$=Table Position (2)

Figure 5:
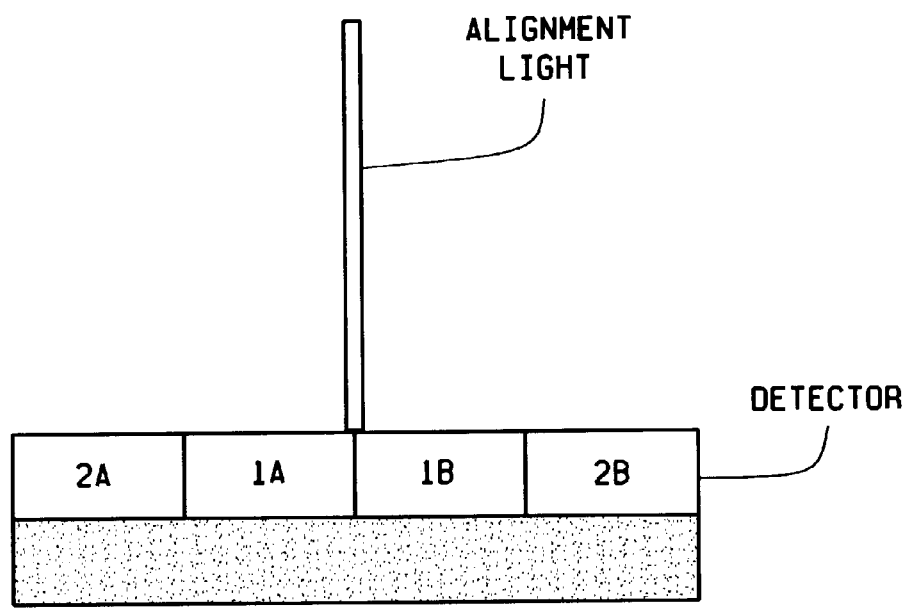
FIG. 5 illustrates an alignment light impinging on a quad detector.

For a two row detector, the slice position is determined in accordance with:

$$S_{Twin}=[-0.5, 0.5]*t \quad (3)$$

where t is the slice thickness and a number from the brackets is used based on which detector is used. For example, for the four row detector, sometimes referred to as a quad system, −1.5, −0.5, 0.5, 1.5 correspond to detectors 2A, 1A, 1B and 2B respectively (see FIG. 5). The slice position is then the sum of the table position and slice displacement or $$S_{position}=\text{Table Position}+S_{twin\ or\ quad} \quad (4)$$

In operation, slice position is already defined in the scan protocol when scan prescription is set.

If a gantry tilt angle is θ, the amount of $Y_{shift}$ in terms of slice displacement and the gantry tilt angle is:

$$Y_{shift}=S_{twin\ or\ Quad}*\tan\theta tm \quad (5)$$

In a quad system, when the slice displacement is ±7.5 mm, the gantry tilt angle is 30°, $Y_{shift}=\pm7.5*\tan(30°)=\pm4.33$ mm. For the two slice system, when the slice displacement is ±5 mm, $Y_{shift}=\pm5*\tan(30°)$ or ±2.89 mm. The largest relative shift (resultant from the top and bottom detector rows) is twice the $Y_{shift}$ for the twin and quad system and is equal to 8.6 mm and 5.78 mm respectively.

In the axial scanning, to compensate for this shift, the image center is shifted in both prospective and retrospective reconstruction. In helical scanning, when the gantry is tilted, projections from different detector macro-rows causes blurriness in helical images. The projection data therefore is shifted along the channel direction in order to compensate for the image center shift. Another center-shifting, $F_{shift}$, is introduced by a helical reconstruction with longitudinal filtration method and is defined as:

$$F_{Shift}=[-n,-n+1\ldots,n-1,n]*(\Delta\beta/2\pi)*(\text{table speed/rotation})*\tan(\theta) \quad (6)$$

In multislice helical scanning, it is necessary to acquire a specific amount of views at the beginning and at the end of a scan range. These additional views are necessary to create the first and last image. The amount of additional views needed is dependent on the collimator configuration, table speed and the selected slice thickness, i.e., the number of additional views needed at the beginning and end of a scan range will increase or decrease depending on these factors. Also, images can be reconstructed retrospectively with different slice thicknesses. As a result, the retrospective images require a different amount of additional views if the desired slice thickness differs from the prospective images.

For a 3:1 helical pitch, and for different smoothing factors, the number of necessary views is set forth below.

| Z-smoothing    | 1x    | 1.04x | 1.33  | 1.5x  | 2x    |
| -------------- | ----- | ----- | ----- | ----- | ----- |
| # of views/image | ~1630 | ~1762 | ~1765 | ~1900 | ~2080 |

For a 6:1 helical pitch, and for different smoothing factors, the number of necessary views is set forth below.

| Z-smoothing    | 1.27x | 1.33x | 1...5 | 2x    |
| -------------- | ----- | ----- | ----- | ----- |
| # of views/image | ~1130 | ~1200 | ~1280 | ~1386 |

The distance needed to generate a single image is determined in accordance with:

[Pitch *f/(Trigger Frequency*Rotation time)]*(#of views)=distance (mm) [7]

The adjustment distance for additional views required for helical scanning is determined in accordance with:

½[Pitch *f/(Trigger Frequency*Rotation time)]*(#of views)=distance (mm) [8]

where f=Collimator configuration, e.g. (4×5) 5 would be f.

In use, the operator specifies the start slice center ("from") and the end slice center ("to") graphically Once set, the system interpolates a straight line between these two points and centers the images along this line. The start slice center handles and end slice center handle only cause movement parallel to the cutline. These handles only move the center of the slice and do not cause slices to be added or deleted. When different centers have been prescribed, the R/L and A/P center fields in the view/edit table for this group display the value for the start slice of this group followed by an asterisk (e.g., 123.5*). If the operator enters a new value in either of these view/edit fields, all images snap back to the same center.

The following images are displayed to the user:

(a) first and last image location, (b) the image interval, (c) the image display field of view (DFOV), (d) the image center location in X/Y plane, and (e) the image tilt (lateral scouts only).

In addition, the system determines, from the user supplied information and selections, the correct data to be used by image reconstruction (helical mode, axial mode with image addition)

If the operator pauses a scan and selects GraphicRx, only groups not yet scanned can be modified. Groups which have been scanned are not be drawn on the localizer. One slice can be prescribed through both the view/edit table and graphically. The cutline width is one pixel.

The following display functions are available when executing GraphicRx:

window/level (preset, trackball, mouse)

next/prior (within the scout series only)

accelerator line list/select

The graphically adjustable parameters may be subject to constraining limits, and when such a limit is reached, the cursor does not move beyond the constraint. An informative message may be posted to the message area.

In an effort to minimize obstructing the scoutview with a cut line, transparent lines could be used. Also, when adding and deleting groups, the mouse is positioned over the view/edit table on the touch screen, and then the protocol can be modified to add or delete group(s). An alternative could be a translucent garbage can to delete group(s) and add icons to add group(s). The user could click on and drag a group into the garbage can to delete a group or drag a "copy" of the add icon onto the scout to add a group. Also, the SFOV (Scan Field of View) image spacing and slice thickness could be modified graphically. For example, a toggle could be provided between showing SFOV and DFOV.

With multiple groups selected, start and end locations adjust such that selected groups which did not overlap prior to the adjustment do not overlap subsequent to the adjustment. The following list of display features are available while in GraphicRx:

list/select (to select a scout from a different series)

zoom/roam measure distance continuous report cursor inverse video auto minify auto enlarge graphic on/off screen save display normal grid user annotation display preferences If the localizer is zoomed or roamed, the cutlines scale with the image. Any cutlines not appearing on the screen due to the scout being zoomed/roamed, are not deleted. Annotation does not need to be shown for 2 or more images at the same location. In this case, a number appears above the cutline on a lateral scout and to the right of the cutline on an A/P scout indicating the number of images at that location.

In accordance with one embodiment of the present invention, host computer 24 determines a true image location in the Z axis, selects a the correct scan data for image generation, and if a scan is initiated via the GUI or via graphic Rx display, determines the affect on the ISO center and DFOV. More particularly, computer 24 determines the offset from the ;can plane for each image plane, so that the true image location in Z is displayed. The image offset from the scan plane is a function of the detector row thickness, the number of detector rows, the scan pitch (helical scanning only), the image thickness, and the gantry tilt angle.

Further, the image thickness is selected by the user via the GUI, and constrains the image interval which is displayed on the graphic Rx display. Based on image thickness and image interval, host computer 24 selects the correct scan data so that images are generated at locations exactly matching those shown on the graphic Rx display. Also, if a scan is prescribed either via the GUI or graphic Rx display, host computer 24 determines the affect on ISO center and DFOV. This information is automatically updated on the graphicRx display by modifying the cut-line position up/down to show ISO affect and by modifying the cut-line length to show DFOV.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method for performing graphic Rx in a multislice imaging system including a display, said method comprising the steps of:

displaying cutlines on a scout display;

enabling an operator to graphically adjust at least one of the number slices, the field of view, and the gantry tilt via the display.

2. A method in accordance with claim 1 wherein displaying cutlines on a scout display comprises the step of displaying at least one of a scout image from a real time scout window, a scout identified in a search, and a last scout displayed for graphic Rx.

3. A method in accordance with claim 1 wherein handles are displayed on the cutlines.

4. A method in accordance with claim 3 wherein a start and an end handle are displayed, and wherein adjusting the number of slices comprises the step of moving the start or end handle.

5. A method in accordance with claim 3 wherein at least one DFOV is displayed, and wherein adjusting the field of view comprises the step of moving the DFOV handle.

6. A method in accordance with claim 3 wherein at least two handles for prescribing gantry tilt are displayed, and wherein adjusting the gantry tilt comprises the step of moving at least one of the gantry tilt handles.

7. A method in accordance with claim 1 further comprising the step of enabling an operator to select one or multiple groups for adjustment.

8. A method in accordance with claim 1 further comprising the step of enabling an operator to adjust at least one of the SFOV, image spacing and slice thickness.

9. Apparatus for performing graphic Rx in a multislice imaging system, said apparatus comprising a processor coupled to a monitor, said processor programmed to:
   display cutlines on a scout display;
   enable an operator to graphically adjust at least one of the number slices, the field of view, and the gantry tilt via the monitor.

10. Apparatus in accordance with claim 9 wherein to display cutlines on a scout display, said processor is programmed to display it least one of a scout image from a real time scout window, a scout identified in a search, and a last scout displayed for graphic Rx.

11. Apparatus in accordance with claim 9 wherein said processor is programmed to display handles on the cutlines.

12. Apparatus in accordance with claim 11 wherein said processor is programmed to display a start and an end handle, and wherein adjusting the number of slices comprises the step of moving the start or end handle.

13. Apparatus in accordance with claim 11 wherein said processor is programmed to display at least one DFOV, and wherein adjusting the field of view comprises the step of moving the DFOV handle.

14. Apparatus in accordance with claim 11 wherein said processor is programmed to display at least two handles for prescribing gantry tilt, and wherein adjusting the gantry tilt comprises the step of moving at least one of the gantry tilt handles.

15. Apparatus in accordance with claim 9 wherein said processor is further programmed to enable an operator to select one or multiple groups for adjustment.

16. Apparatus in accordance with claim 9 wherein said processor is further programmed to enable an operator to adjust at least one of the SFOV, image spacing and slice thickness.

17. A computed tomography imaging system, comprising:
   an x-ray source;
   a detector aligned with said x-ray source and comprising multiple detector cells extending along a z-axis, said detector configured to collect multiple slices of data;
   a scalable data acquisition system coupled to said detector and configured to convert signals received from said detector to digital form;
   a slip ring coupled to said data acquisition system;
   a scan and reconstruction control unit coupled to said slip ring and configured to generate image data from data transmitted thereto from said data acquisition system via said slip ring; and
   a host computer coupled to said scan and reconstruction control unit, said host computer comprising a user interface for enabling a user to perform graphic Rx, said host computer comprising a processor coupled to a monitor, said processor programmed to:
   display cutlines on a scout display; and
   enable an operator to graphically adjust at least one of the number slices, the field of view, and the gantry tilt via the monitor.

18. A system in accordance with claim 17 wherein to display cutlines on a scout display, said processor is programmed to display at least one of a scout image from a real time scout window, a scout identified in is search, and a last scout displayed for graphic Rx, and wherein said processor is programmed to display handles on the cutlines.

19. A system in accordance with claim 17 wherein said processor is further programmed to:
   display a start and an end handle, and adjusting the number of slices comprises the step of moving the start or end handle;
   display at least one DFOV, and adjusting the field of view comprises the step of moving the DFOV handle;
   display at least two handles for prescribing gantry tilt, and adjusting the gantry tilt comprises the step of moving at least one of the gantry tilt handles.

20. A system in accordance with claim 17 wherein said processor is further programmed to enable an operator to select one or multiple groups for adjustment.

* * * * *